(12) United States Patent
Grumstrup

(10) Patent No.: US 10,890,298 B2
(45) Date of Patent: Jan. 12, 2021

(54) LIQUID DETECTION DEVICE WITH WIRELESS COMMUNICATOR

(71) Applicant: FISHER CONTROLS INTERNATIONAL LLC, Marshalltown, IA (US)

(72) Inventor: Bruce F. Grumstrup, Marshalltown, IA (US)

(73) Assignee: FISHER CONTROLS INTERNATIONAL LLC, Marshalltown, IA (US)

( * ) Notice: Subject to any disclaimer, the term of this patent is extended or adjusted under 35 U.S.C. 154(b) by 401 days.

(21) Appl. No.: 15/258,075

(22) Filed: Sep. 7, 2016

(65) Prior Publication Data

US 2018/0066804 A1    Mar. 8, 2018

(51) Int. Cl.
*F17D 5/00* (2006.01)
*G01N 33/00* (2006.01)
(Continued)

(52) U.S. Cl.
CPC ............ *F17D 5/005* (2013.01); *F04B 43/009* (2013.01); *G01M 3/04* (2013.01); *G01N 1/2247* (2013.01); *G01N 33/0036* (2013.01); *G01N 33/0062* (2013.01); *G08B 21/20* (2013.01); *H04Q 9/00* (2013.01); *H04W 4/80* (2018.02); *H04Q 2209/43* (2013.01); *H04Q 2209/823* (2013.01); *H04Q 2209/826* (2013.01); *H04Q 2209/88* (2013.01); *H04W 84/12* (2013.01)

(58) Field of Classification Search
CPC .......................... F17D 5/005; G01N 33/0036
See application file for complete search history.

(56) References Cited

U.S. PATENT DOCUMENTS

| 5,501,577 A | 3/1996 | Cornell et al. |
| 2010/0085155 A1 | 4/2010 | Boss et al. |

(Continued)

FOREIGN PATENT DOCUMENTS

WO    WO-01/36848 A1    5/2001

OTHER PUBLICATIONS

International Search Report for PCT/US2017/049803, dated Nov. 20, 2017.
Written Opinion for PCT/US2017/049803, dated Nov. 20, 2017.

*Primary Examiner* — Walter L Lindsay, Jr.
*Assistant Examiner* — Andrew V Do
(74) *Attorney, Agent, or Firm* — Marshall, Gerstein & Borun LLP

(57) ABSTRACT

Devices, systems, and methods of detecting and providing an alert regarding the presence of liquid contamination in a pneumatic supply line and/or in a pneumatic instrument are described. A liquid detection device configured to be coupled to the pneumatic supply includes an electronic liquid sensor configured to detect the presence of liquid in the pneumatic supply and a wireless communicator configured to transmit data from the electronic liquid sensor to a wireless communication node. The liquid detection device may be installed at different locations along a pneumatic supply in a plant. The plant network can forward the transmitted message from the communication node onto a plant computer, where and alert or other message may be provided to an operator or other computer system when water or other liquid is detected.

26 Claims, 4 Drawing Sheets

(51) Int. Cl.
*G08B 21/20* (2006.01)
*H04W 4/80* (2018.01)
*H04Q 9/00* (2006.01)
*G01M 3/04* (2006.01)
*G01N 1/22* (2006.01)
*F04B 43/00* (2006.01)
*H04W 84/12* (2009.01)

(56) References Cited

U.S. PATENT DOCUMENTS

| | | | |
|---|---|---|---|
| 2015/0016001 A1* | 1/2015 | Quirk | H02H 5/083 361/78 |
| 2015/0045970 A1* | 2/2015 | Anderson | F16K 37/0083 700/282 |
| 2015/0276441 A1* | 10/2015 | Kraige | G01F 1/88 73/861.42 |

* cited by examiner

LIQUID DETECTION DEVICE WITH WIRELESS COMMUNICATOR

FIELD

This application relates generally to a liquid detection device with a wireless communicator, and more particularly, a liquid detection device configured to detect and provide an indication of liquid contamination in a pneumatic supply.

BACKGROUND

In an industrial plant with process control systems, it is common to use compressed air for many different applications, including for example driving the movement of various pieces of control equipment, such as valves, regulators, and valve controllers. A plant air distribution system typically includes one or more air compressors located in and/or around the vicinity of the primary plant equipment and a distribution system of pneumatic lines extending through various areas of the plant that provide compressed air at the locations needed throughout the plant.

Many pieces of pneumatic control equipment that use or generate the compressed air of the plant air, such as digital valve controllers and pneumatic process controllers for example, may be susceptible to damage or performance degradation if water or other liquid is present in the compressed air being supplied to the piece of equipment. However, because the pneumatic supply in the plant air and the individual piece of equipment is generally a closed system, it can be difficult to know if a problematic amount of water or other liquid is present in the air lines and/or the individual pieces of equipment.

In order to alleviate the buildup of water and other liquid in pneumatic lines and/or equipment, liquid traps and/or drains may be installed at selected locations along the pneumatic lines and/or in a particular piece of control equipment. For example, a liquid drain valve may be installed in an elbow along a low point of an air line. In another example, a pneumatic filter regulator may be provided with a liquid drain valve in the bottom of a drip well that collects and drains liquid drawn out of air going through the regulator. Although these arrangements may help remove or reduce the problem of unwanted liquids from the plant air supply, they may not provide any indication to the plant operators of a change in the system that may point to the need for preventive maintenance or repair.

SUMMARY

According to some aspects, a device, system, and/or method to detect and provide an indication, such as an alert or other indication, of liquid contamination in a pneumatic supply may wirelessly transmit data from an electronic liquid sensor. In this way, it may be easier to retrofit such a device, system, and/or method into an existing plant pneumatic system.

According to some aspects, a device, system, and/or method to detect and provide an indication of liquid contamination may transmit the data to a communication node on a plant computer network. In this way, delivery of relevant data or alerts or other indications to operations personnel or other computer systems over existing communication networks in the plant may be realized.

According to some aspects, a device, system, and/or method detects and provides a warning of the presence and/or amount of liquid contamination in a pneumatic supply line and/or in a pneumatic instrument. This may help operators decide when to perform maintenance on the pneumatic supply line and/or the pneumatic instrument.

One or more of these aspects may be realized in any one or more of the following arrangements.

In some arrangements, a liquid detection device to detect and provide an indication of liquid contamination in a pneumatic supply includes an electronic liquid sensor and a wireless communicator. The electronic liquid sensor may be configured to be coupled to a pneumatic supply and to detect the presence of liquid in the pneumatic supply. The wireless communicator may be configured to transmit data from the electronic liquid sensor to a communication node on a plant computer network.

In some arrangements, a process control system includes a liquid detection device with a wireless communicator according to the present disclosure. The process control system may include a pneumatic supply line, which may be, for example, in a process plant. The liquid detection device may be operatively coupled to the pneumatic supply line to sense the presence of liquid in the pneumatic supply. A wireless communication node may be provided, for example on a plant computer network. The wireless communicator may be configured to transmit data from the electronic liquid sensor to the wireless communication node.

In some arrangements, a method of monitoring a pneumatic supply in a process control system for liquid includes detecting the presence of liquid in the pneumatic supply with an electronic liquid sensor and transmitting with a wireless communicator a wireless signal that is indicative of the presence of liquid detected by the electronic liquid sensor to the wireless communication node on the plant computer network.

Any one of these aspects and/or arrangements may further include any one or more of the following optional arrangements and/or features.

The wireless communicator may be a near-field data transmitter. The near-field data transmitter may have a transmission range of less than about 100 feet, such as, for example any transmission range between about 100 feet and 0 feet. For example, the near-field data transmitter may be or include a Bluetooth transmitter and/or a Wi-Fi transmitter. However, other types of wireless transmission are also possible. Preferably, the wireless communicator is a low-power transmitter so as to minimize power usage. In this way, the lifespan of a battery power source, if used, may be lengthened.

The wireless communicator may be configured to communicate via a wireless digital industrial automation protocol, such as Wireless HART or ISA 100.11a protocols. Other digital industrial automation protocols may also be used.

The electronic liquid sensor may include a water sensor configured to detect the presence of water in the pneumatic supply. Any suitable type of water sensor may be used, such as a Wheatstone bridge or other resistive trace sensor, for example.

The electronic liquid sensor may include detection circuitry connected to the liquid sensor configured to detect the amount of liquid present. Any suitable type of detection circuitry may be used.

The electronic liquid sensor may include power circuitry configured to control a supply of power to the detection circuitry and the wireless communicator. Any suitable type of power circuitry may be used.

The liquid detection device may include a battery power source configured to power the electronic liquid sensor and/or the wireless communicator. The battery power source may be carried by a housing of the liquid detection device. However, other power sources could also be used. For example, power for the electronic liquid sensor and/or the wireless communicator may be provided from a nearby field device, a power bus in the plant, or other direct-wired power source.

The electronic liquid sensor and the wireless communicator may be carried together as a single unit by a housing. The housing may be divided into different portions that are connected together. The water sensor may be disposed in a first portion of the housing exposed to the pneumatic supply, such as a sensor body. The detection circuitry, power circuitry, battery, and wireless communicator may be disposed other areas of the housing that are fluidly sealed from the first portion of the housing, such as an electronics housing. This may provide a convenient package and form factor for quickly and easily coupling to various plant air supplies, such as pneumatic lines, and/or pneumatic equipment. This may be particularly convenient for retrofitting to existing installed pneumatic equipment and/or pneumatic lines.

The wireless communicator may be configured to transmit the data intermittently. For example, the wireless communicator may be configured to transmit the data at preselected time intervals and/or in response to the presence of water or other liquid. This may conserve power, which could increase the lifespan of a battery power source, for example.

The wireless communicator may be configured to transmit the data at a first pre-selected time interval in response to the electronic liquid sensor sensing less than a threshold amount of liquid and to transmit the data at a second, shorter time interval in response to the electronic liquid sensor sensing more than the threshold amount of liquid. For example, the wireless communicator may be configured to transmit data from the liquid sensor once a day (or some other pre-selected time interval) to conserve power during most operating periods, and when some threshold amount of liquid is sensed, the wireless communicator may then transmit data from the liquid sensor more frequently, such as three or four times a day, or once an hour, minute, or second, and so on, to provide increased reporting when a potentially problematic water or other liquid infiltration occurs.

The electronic liquid sensor may be configured to differentiate between no liquid being present and one, two, or more different levels of liquid being present. The wireless communicator may be configured to transmit a first message when liquid is detected and a second message when liquid is not detected. The wireless communicator may be configured to transmit a first message when no liquid is present, a second message a first level of liquid is present, and a third message when a second level of liquid is present. This may help operators or other watch systems differentiate between different levels of water present, which in turn may provide additional information for deciding if and when maintenance should be performed on the pneumatic system components to correct a water infiltration problem.

The electronic liquid sensor may be periodically activated temporarily to sense for the presence of liquid in the pneumatic supply, or the electronic liquid sensor may be activated continuously. The electronic liquid sensor may be periodically activated at a pre-selected interval regardless of the presence of liquid detected by the electronic liquid sensor. Alternatively, the interval may change depending on detection of liquid by the electronic liquid sensor. The electronic liquid sensor may be activated at a first pre-selected time interval when no liquid is detected, and at a second, faster time interval when liquid is detected.

A wireless signal may be transmitted by the wireless communicator corresponding with and/or in response to each activation of the electronic liquid sensor. The signal transmitted from the communication node may be relayed from the communication node to a plant computer on the plant network. This may enable operators or other system processes to be alerted to the presence of liquid in the pneumatic lines and/or equipment.

The wireless communication node may be disposed in various locations throughout a plant and/or in along a computer network. The wireless communication node may be part of a field device configured to communicate on a digital industrial automation protocol, such as HART or FOUNDATION fieldbus or Profibus, on a plant computer network. For example, the field device may be a digital valve controller or some other "smart" communicating piece of process control equipment. However, the wireless communication node is not necessarily part of a field device. Rather, the wireless communication node may be a stand-alone data communications transceiver, such as a Wi-Fi or a Bluetooth transceiver or a Wireless HART transceiver, connected to a plant computer network.

A liquid detection device, system, and/or method in accordance with the present disclosure may be easier to retrofit to existing plant air supplies, such as pneumatic lines and/or pneumatic equipment. It may be easier to customize the liquid detection device, system, and/or method to suit a particular installation arrangement, thereby providing improved flexibility. Multiple liquid sensors may be able to communicate with a single communication node, such as a wireless smart field device or communication transceiver and/or a liquid sensor may be able to communicate with several different communication nodes. A liquid detection device with a wireless communicator may make it easier to install in and around explosive or other hazardous areas by reducing or eliminating wired connections from the liquid sensor to a communication node in a plant.

These and other aspects, arrangements, features, and/or technical effects will become apparent upon detailed inspection of the figures and the following description.

DETAILED DESCRIPTION

Figure 1:
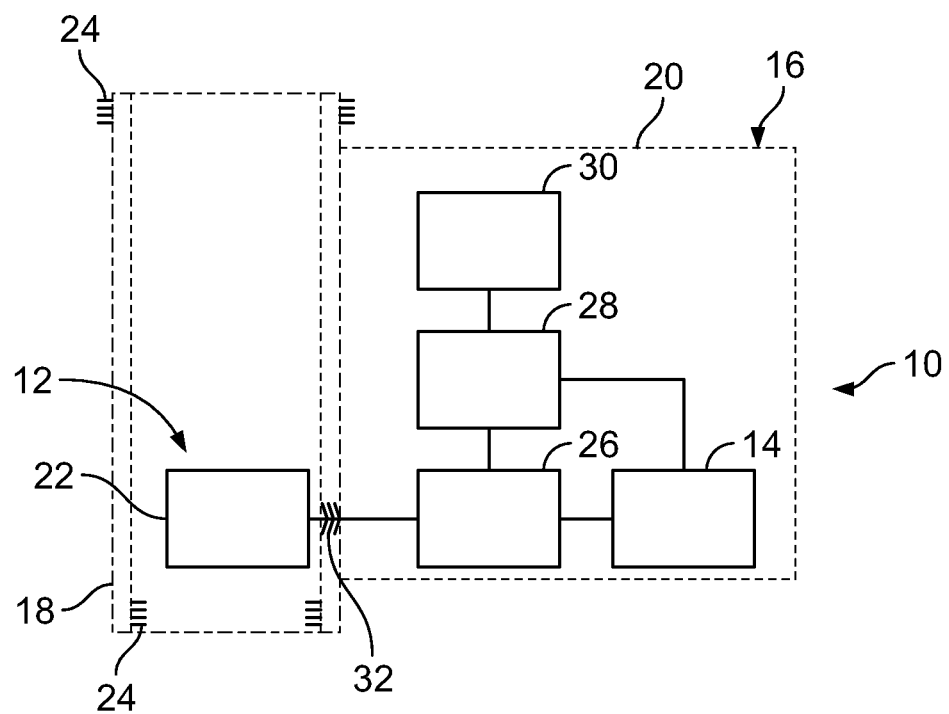
FIG. 1 is a schematic diagram of a liquid detection device to detect and transmit an indication of liquid contamination in a pneumatic supply according to aspects of the present disclosure.

Turning now to the exemplary arrangements of the drawings, FIG. 1 illustrates an exemplary liquid detection device 10 according to aspects of the disclosure. The liquid detection device 10 includes an electronic liquid sensor 12 and a wireless communicator 14. The liquid detection device 10 is configured to detect the presence of liquid contamination in a pneumatic supply, for example, water in a plant air line or a piece of pneumatic equipment. In addition, the liquid detection device 10 is configured to transmit data, for example including an alert or other indication to a plant operator or a computer system within a plant, regarding whether liquid contamination is detected in the pneumatic supply. In particular, the electronic liquid sensor 12 is configured to detect the presence of water or other liquid in the pneumatic supply, and the wireless communicator 14 is configured to transmit data from the electronic liquid sensor 12 wirelessly, for example with Wi-Fi, Bluetooth. or Wireless HART transmissions. By using a wireless communicator 14 to transmit the data from the electronic liquid sensor 12, the liquid detection device 10 can be more easily retrofitted into existing process control systems without having to connect additional communication wires between the liquid detection device 10 and a communication node in the process control network.

The wireless communicator 14 is preferably a near field data transmitter. For example, the wireless communicator 14 may be a low power transmitter, such as a Bluetooth transmitter and/or a Wi-Fi transmitter. The wireless communicator 14 is preferably also a relatively low power transmitter. Thus, in many arrangements, the wireless communicator 14 may be a near field data transmitter with a transmission range of less than about 100 feet, and may have a transmission range of less than 50 feet, 20 feet, 10 feet, or even less, depending upon the specific location of the preferred communication node for receiving wireless transmissions from the wireless communicator 14. However, other types of longer distance wireless transmitters may be used.

The wireless communicator 14 may be configured to communicate on a wireless digital industrial automation protocol. Some exemplary digital industrial automation protocols include wireless HART and ISA 100.11 communication protocols. However, the wireless communicator 14 may be configured to communicate on other digital communication protocols. In this way, the wireless communicator 14 can be configured to communicate with a plant computer network, for example, within an industrial process plant or other type of industrial plant. This allows the wireless communicator 14 to send data transmissions relative to the status of the electronic liquid sensor 12 along existing plant digital communication networks. Thus, for example, the wireless communicator 14 can send alerts, such as warnings or status information, to operations personnel at a remote location via the plants digital communication networks if water or other liquid is sensed by the electronic liquid sensor 12.

The liquid detection device 10 preferably has a housing 16 that contains and/or carries the electronic liquid sensor 12 and the wireless communicator 14 together as a single unit. Further, the housing 16 preferably encloses the electronic circuits of the electronic liquid sensor 12 and the wireless communicator 14 in such a manner that would be suitable for use in explosive and/or other hazardous flammable conditions. In some arrangements, the liquid detection device 10 may be intrinsically safe.

The housing 16 includes a sensor body 18 and an electronics case 20. The sensor body 18 is configured to be operatively coupled to a pneumatic supply, such as a pneumatic line or pneumatic device, so as to detect moisture, for example from water or other liquids entrained within the air running through the line and/or device. The electronics case 20 encloses the primary electronics components of the electronic liquid sensor 12 and the wireless communicator 14, preferably in an airtight manner so as to minimize and/or eliminate the risk of igniting a flammable environmental atmosphere. However, the liquid detection device 10 is not limited to this arrangement of the housing 16, but rather may take any form suitable for carrying the electronic liquid sensor 12 and the wireless communicator 14 together as a single unit.

The sensor body 18 may take different forms specifically adapted for particular pneumatic supplies. One common form of a sensor body 18 is shown in FIG. 1, in which the sensor body 18 includes a short tube section configured to be attached to an air supply with a water sensor 22 disposed inside the tube section. Thus, the water sensor 22 can sense the presence of water (or other liquids) in the air that passes through or collects in the interior of the tube section. The tube section can be configured to attach to many different arrangements of pneumatic supplies. For example, the tube section may include connectors 24, such as threads, clamps, nipples, and/or other connector fittings, at one or both ends so as to be connected in-line along a pneumatic line or with a pneumatic supply. However, in some arrangements, one end of the tube section may have a closed end and the other end may have a connector 24, such that the sensor body 18 forms a plug member that can be connected to a pneumatic supply. In other arrangements, the tube section may omit any connectors 24. However, in any arrangement, the sensor body 18 is configured to be operatively connected to the pneumatic supply so as to direct the air into the interior of the sensor body so as to engage the water sensor 22, so that the water sensor 22 can sense the presence of liquid in the air supply.

The electronic liquid sensor 12 in this arrangement includes the water sensor 22, detection circuitry 26, and power circuitry 28. The water sensor 22 may be any type of sensor suitable for detecting the presence and/or amount of water in the pneumatic supply. For example, the water sensor 22 may be a conductive trace sensor, such as a Wheatstone bridge sensor. However, other types of water sensors may be used. Preferably, the water sensor 22 is suitable for safe use in potentially flammable or explosive atmospheres. The detection circuitry 26 may take any form of electrical circuitry configured to run the water sensor 22, to identify the presence and/or amount of water detected by the water sensor 22, and to generate data representative of the presence and/or amount of water detected in a form suitable to be transmitted by the wireless communicator 14 in accordance with the functionalities described herein. Thus, the detection circuitry 26 is connected to the water sensor 22 in order to obtain readings from the water sensor and is connected to the wireless communicator 14 in order to provide generated data responsive to the obtained readings to the wireless communicator 14 for transmission. The power circuitry 28 may take any form of electrical circuitry configured to provide suitable power delivered from a power supply to operate the detection circuitry 26 and to operate the wireless communicator 14. In some arrangements, the detection circuitry 26 and/or the power circuitry 28 may be implemented with appropriate ASIC chips or other circuitry.

In this arrangement, the power supply for the power circuitry 28 is supplied by a battery 30. However, other forms of electrical power supply may be used. For example, the electronics module 16 could include a connection for connecting to the power supply of a nearby field device, power loop, or bus. In another example, the electronics module could be hardwired to a dedicated power source. Using the battery 30, however, also helps improve the ease of retrofitting the liquid detection device 10 into an existing process control system by eliminating the need for additional power wires to be connected to a power source.

The water sensor 22 is disposed in a first portion of the housing 16 that is exposed to the pneumatic supply (e.g., the sensor body 18), and the detection circuitry 26, power circuitry 28, battery 30, and wireless communicator 14 are disposed in one or more other areas of the housing 16 that are fluidly sealed from the first portion of the housing (e.g., the electronics case 20). In the exemplary arrangement, each of the battery 30, the detection circuitry 26, the power circuitry 28, and the wireless communicator 14 is contained within the electronics case 20. Thus, the housing 16 contains all the portions of the electronic liquid sensor and the wireless communicator together as a single unit in a form factor that is easy to handle and easy to install to an existing pneumatic line and/or piece of pneumatic equipment. Preferably, the electronics case 20 is sealed so as to prevent ingress of water, hazardous atmosphere, and/or other undesirable substances that may negatively affect the electronics of the electronic liquid sensor 12 and the wireless communicator 14. The water sensor 22 is exposed to the pneumatic supply and any liquids therein in order to sense liquid in the pneumatic supply. However, the water sensor 22 is preferably fluidly sealed from the remaining portions of the electronics, for example by a liquid and pneumatic tight seal 32 around the electrical connection between the water sensor 22 and the detection circuitry 26 through the wall of the sensor body 18 and/or the wall of the electronics case 20. However, other arrangements of protecting the electronic circuits from water may be used.

The wireless communicator 14 may be configured to transmit data continuously or intermittently. Preferably, the wireless communicator 14 is configured to transmit data intermittently, which can help conserve power and/or extend the life of a battery 30, if used, and thereby reduce maintenance requirements of the liquid deck text device 10.

In some arrangements, the wireless communicator 14 is configured to transmit data at one or more pre-selected time intervals. The pre-selected time interval may be selected to meet any of various design criteria, and could for example be any selected value between a few milliseconds and days, weeks, or months, depending upon particular design parameters. In other arrangements, the time interval between transmissions from the wireless communicator 14 may vary depending upon the presence of and/or amount of liquid detected by the water sensor 22. In some arrangements the time interval between transmissions may vary between different pre-selected time intervals. For example, the wireless communicator 14 may transmit at a first, longer pre-selected time interval if no liquid is sensed by the water sensor 22 (such as once every hour or day), and at a second, shorter pre-selected time interval (such as once every 5 minutes or half day) if liquid is sensed by the water sensor 22.

The pre-selected time interval for transmissions can be constant regardless of what is sensed by the water sensor 22, i.e., the time interval does not change or otherwise depend upon what is sensed by the water sensor 22. For example, the wireless communicator 14 may be configured to transmit a message relative to whether and/or how much water is sensed by the water sensor 22 corresponding with every pre-selected time interval, such as each second, minute, hour, day, week, month, etc. The message transmitted by the wireless communicator 14 may vary depending upon what is sensed by the water sensor 22. In order to do this, the electronic liquid sensor 12 and detection circuitry are configured to differentiate between not only the presence or lack of water in the pneumatic supply, but also at least two (or more) different amounts and/or levels of water in the pneumatic supply. Thus, for example, the wireless communicator 14 may transmit a first message indicating that no water is present in the pneumatic supply, a second message indicating that a small amount of water is present, or a third message indicating that a large amount of water is present, depending on and corresponding to the level of water (or other liquid) sensed by the water sensor 22. In this way, the liquid detection device 10 can conserve power as described above without increasing the frequency of the transmissions from the wireless communicator 14 and also provide more data rich information to an operator or maintenance system that could help differentiate between small and/or insignificant accumulations of liquid and large and/or potentially damaging accumulations of liquid in the pneumatic supply.

Although the wireless communicator 14 may be configured to transmit different messages depending upon the amount and/or level of water detected by the water sensor 22, alternatively the wireless communicator 14 may be configured to transmit a message that only indicates whether liquid is detected or not detected by the water sensor 22. In this case, the change in the time interval between transmissions would provide additional data to an operator or maintenance system relative to how significant the sensed liquid may be relative to possible maintenance requirements.

The liquid detection device 10 may be configured to be used with different types of equipment and/or in different locations throughout a process control or other industrial plant. Following are some exemplary arrangements that exemplify the versatility of the liquid detection device 10.

Figure 2:
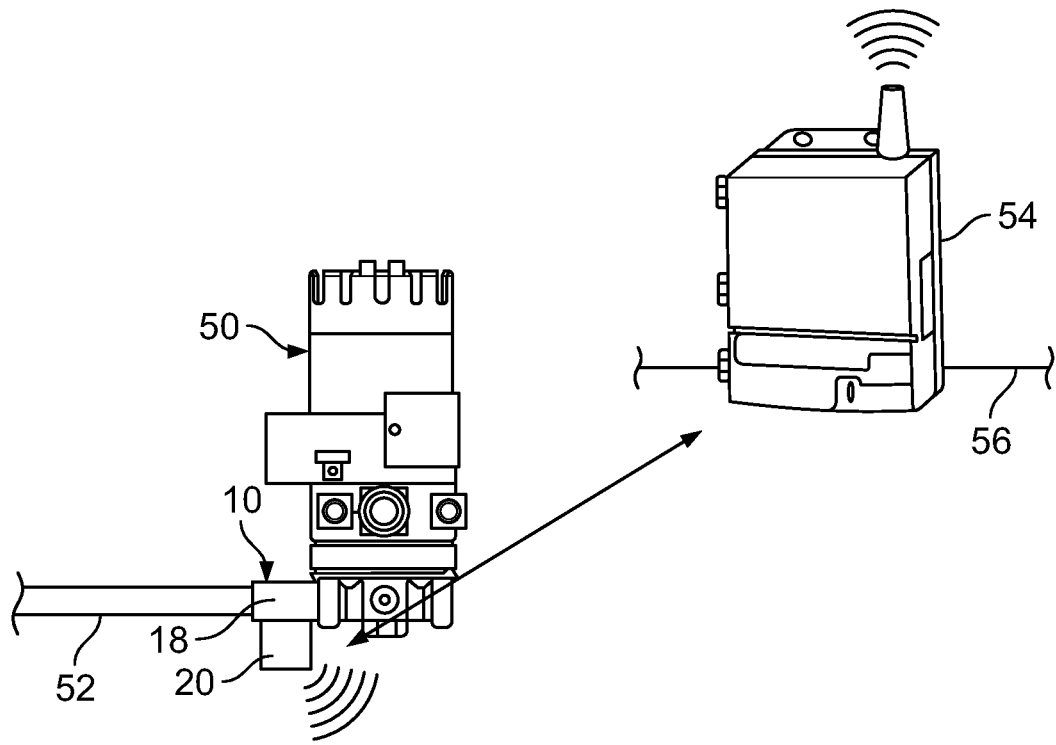
FIG. 2 is a schematic diagram of portions of a process control system with the liquid detection device installed on a non-communicating pneumatic process control device.

FIG. 2 illustrates a portion of a process control system in which the liquid detection device 10 is operatively installed on a non-communicating pneumatic device 50. The pneumatic device 50 could be any piece of pneumatic equipment that does not include a wireless receiver capable of receiving (and decoding) the transmissions sent by the wireless communicator 14. The pneumatic device 50 may have "smart" data communication capabilities or may not, such as a pneumatic valve actuator or similar device that does not communicate data messages with a plant operating computer. Here, the liquid detection device 10 is coupled in-line with a pneumatic supply line 52 that supplies air pressure from the plant air. One end of the sensor body 18 is coupled to an air inlet for the pneumatic supply into the pneumatic device 50. The other end of the sensor body 18 is coupled to the pneumatic supply line 52, such that compressed air from the pneumatic supply line 52 goes through the sensor body 18 and into the pneumatic device 50 in order to drive the pneumatic device 50. In this arrangement, because the pneumatic device 50 does not have a wireless receiver and/or is not configured for "smart" data communication (e.g., does not have a HART or FOUNDATION fieldbus or similar communicator) on a plant computer network, the liquid detection device 10 communicates with a wireless communication node 54, such as a Wi-Fi router, that is remote from the pneumatic device 50. For example, the wireless communication node 54 may be in a central location for that area of the plant within the transmission range of the wireless communicator 14 and may be connected to a communication platform, such as a bus or wireless network, for data communication between plant computers. In this arrangement, the wireless communicator 14 may be configured and/or selected for transmitting data the necessary distance to one or more such remote wireless communication nodes 54. If possible, the wireless communicator 14 is preferably a near-field and/or low power transmitter. However, if a near field transmitter would be insufficient to traverse the distance between the location of the liquid detection device 10 and the nearest remote communication node 54, a different transmitter sufficient to traverse the necessary distance could be used, such as a long-distance or mid-range and/or higher power transmitter. In any event, when the electronic liquid sensor 10 senses some predefined minimum threshold of liquid in the pneumatic supply of the pneumatic line 52 (as described previously), the wireless communicator 14 is configured to send an indication wirelessly, which can be received at the communication node 54, and subsequently forwarded (i.e., transmitted further) from the communication node 54 along a plant network 56 to one or more plant computers, which may be configured to provide the indication to an operator or other control or monitoring computer system.

Figure 3:
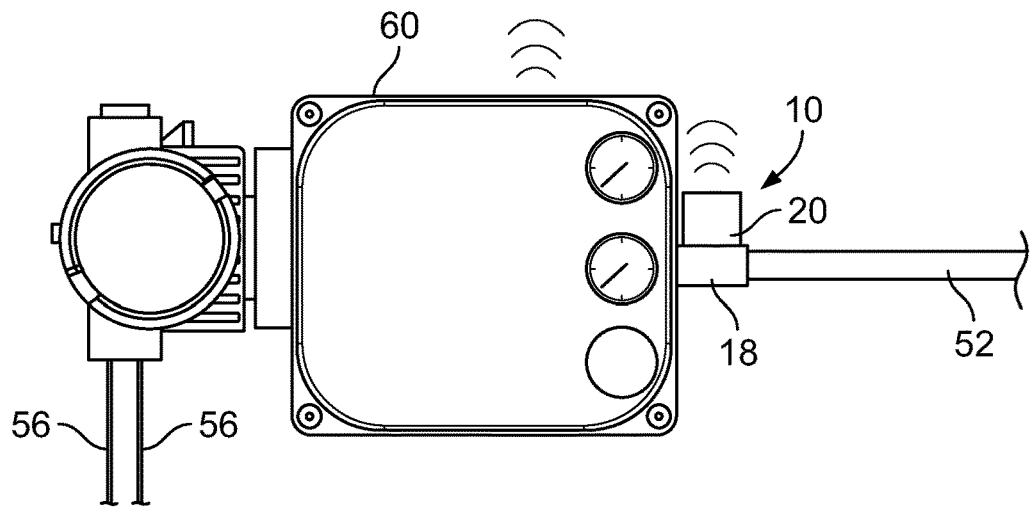
FIG. 3 is a schematic diagram of portions of a process control system with the liquid detection device installed on a communicating pneumatic process control device.

FIG. 3 illustrates a portion of a process control system in which the liquid detection device 10 is operatively installed on a pneumatic device 60 that also has a wireless receiver capable of receiving wireless transmissions from the wireless communicator 14. The pneumatic device 60 is also a "smart" device that includes a communicator for communicating data along a plant network, such as 56. For example, the pneumatic device 60 may be a digital valve controller configured with a HART or FOUNDATION fieldbus (or similar) communication. Similar to the arrangement in FIG. 2, the liquid detection device 10 is coupled in-line with a pneumatic supply line 52 with one end of the sensor body 18 coupled to an air inlet into the pneumatic device 60 and the other end of the sensor body 18 coupled to the pneumatic supply line 52, such that compressed air from the pneumatic supply line 52 goes through the sensor body 18 and into the pneumatic device 60. In this arrangement, however, because the pneumatic device 60 has a wireless receiver and can communicate across the plant network, the liquid detection device 10 may be configured to communicate directly with the pneumatic device 60. Therefore, because the distance between the liquid detection device 10 in the receiver on the pneumatic device 60 is relatively short, for example, less than 10 feet, less than 5 feet, or even less than 1 foot, the wireless communicator 14 may be a near-field transmitter and/or a low-power transmitter, such as a Bluetooth transmitter, thus saving additional power and increasing the life span of the battery 30 (if used). Similarly as above, when the electronic liquid sensor 10 senses some predefined minimum threshold of liquid in the pneumatic supply of the pneumatic line 52 (as described previously), the wireless communicator 14 is configured to send an indication wirelessly, which can be received at the pneumatic device 60, which acts as a communication node on the plant network, and subsequently forwarded from the pneumatic device 60 along the plant network 56 to one or more plant computers, which may be configured to provide the indication to an operator or other control or monitoring computer system.

Figure 4:
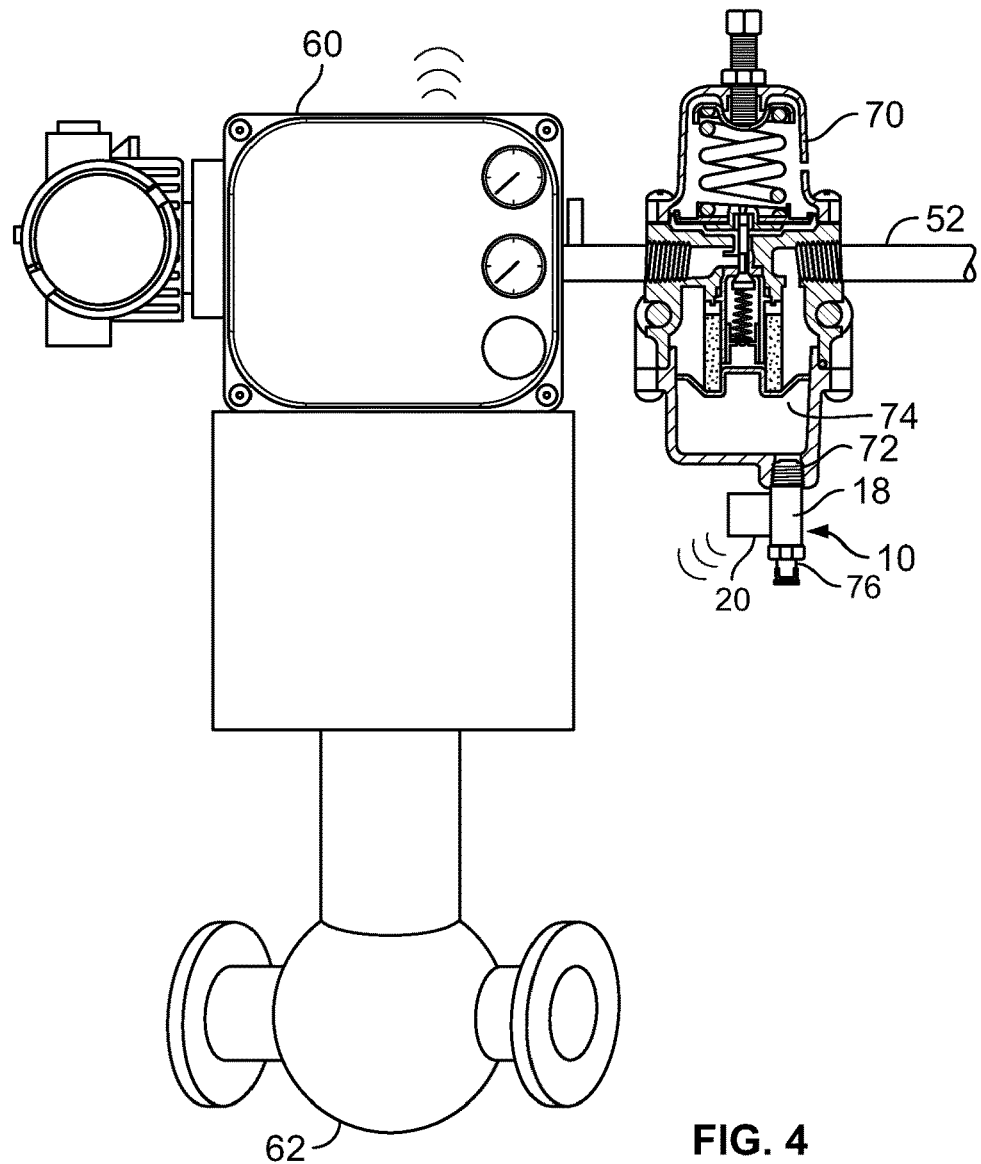
FIG. 4 is a schematic diagram of the liquid detection device operatively coupled to a pneumatic filter regulator for a digital valve controller in a process control system.

FIG. 4 illustrates another exemplary installation arrangement in a portion of a process control system, in which the liquid detection device 10 is operatively attached to a pneumatic filter regulator 70, which is in turn attached to the air inlet of a digital valve controller 60 for an actuator and valve 62. In this arrangement, the sensor body 18 is operatively connected in a drain hole 72 from a drip well 74 of the pneumatic filter regulator 70. In particular, one end of the sensor body 18 is attached, for example by threads, into the drain hole 72, and a standard drain plug 76, which may optionally include a drain release valve 76, is coupled to the opposite end of the sensor body 18. Thus, in this arrangement, the liquid detection device 10 forms more of a plug member for the drain 72 rather than an in-line coupling along the pneumatic line 52. Similar to the arrangement of FIG. 3, although the liquid detection device 10 is not attached directly to the digital valve controller 60, it is still relatively close, such as within than 10 feet or less from the wireless receiver of the digital valve controller 60. Thus, the wireless communicator 14 again may be a near-field and/or low-power transmitter that transmits to the digital valve controller 60.

Although specific exemplary installation arrangements are described with regard to FIGS. 2-4, the liquid detection device 10 is not limited to these particular installation arrangements, but rather may be configured for and/or installed in an almost unlimited number of arrangements within a plant. In particular, one technical advantage of the liquid detection device 10 is the increased flexibility for configuration for an installation in many different particular arrangements throughout a plant.

Figure 5:
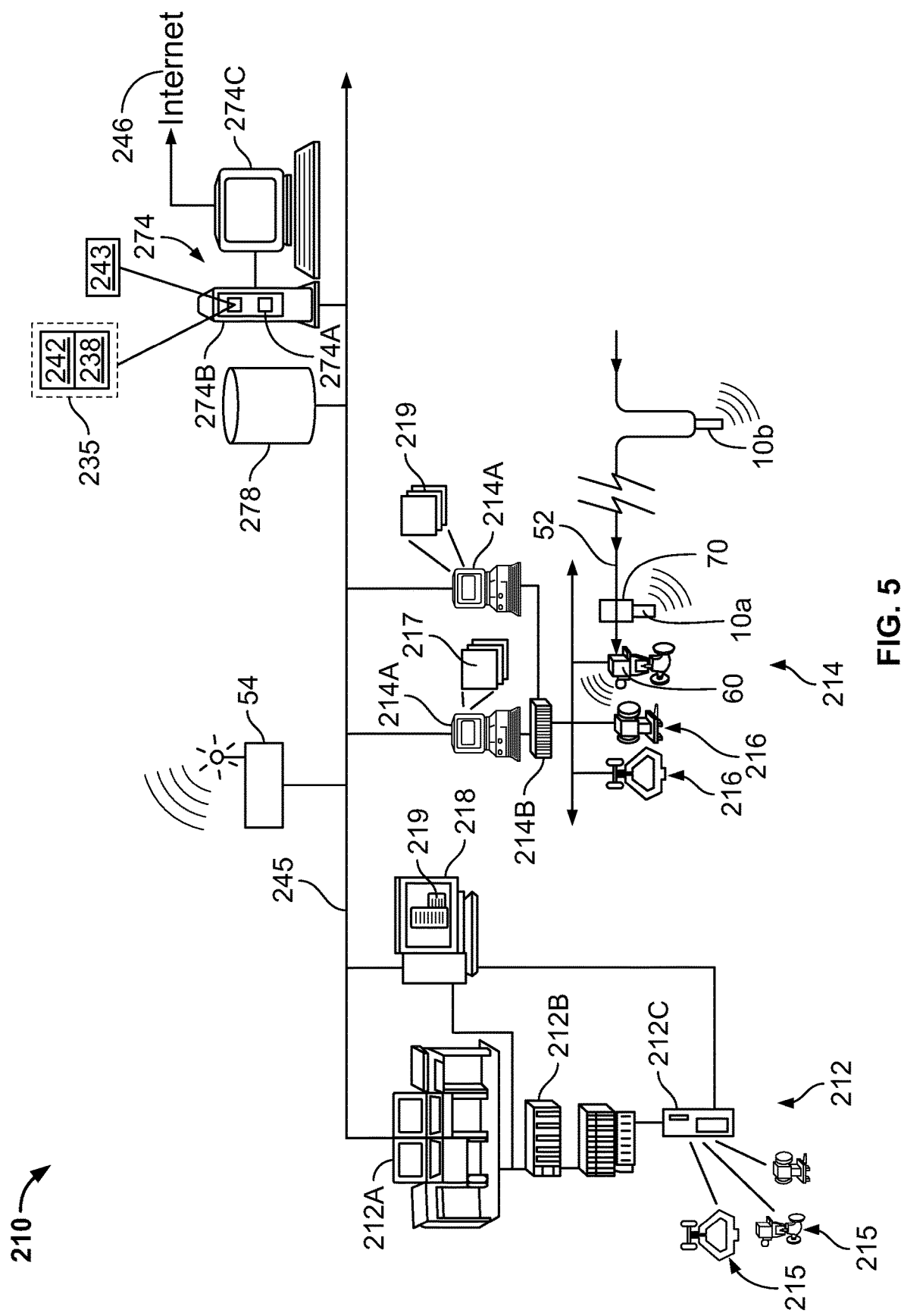
FIG. 5 is a schematic diagram of an exemplary process control system outfitted with liquid detection devices of the present disclosure.

FIG. 5 illustrates an exemplary process control system that implements liquid detection sensors 10 such as those described above in various installations. An example process plant 210 may include a number of control and maintenance systems interconnected together with supporting equipment via one or more communication networks, which are described in further detail hereinafter. In this example, two different liquid detection sensors 10a and 10b are illustrated in the process plant. However more or fewer liquid detection sensors 10 may be operatively installed around the process plant. The liquid detection sensor 10a is connected to a pneumatic filter regulator 70 for a digital valve controller 60, which is in turn operatively connected to plant air by the pneumatic line 52, generally as described with respect to FIG. 4. The liquid detection sensor 10b is operatively connected to a low point along the pneumatic line 52 where water and other liquid contaminates could collect, such as at a water trap as illustrated in FIG. 5 or in a header or elsewhere.

The process plant 210 may include one or more process control systems 212 and 214. The process control system 212 may be a traditional process control system such as a PROVOX or an RS3 system or any other control system which includes an operator interface 212A coupled to a controller 212B and to input/output (I/O) cards 212C which, in turn, are coupled to various field devices such as analog (e.g., 4-20 mA) and Highway Addressable Remote Transmitter (HART®) field devices 215. The process control system 214, which may be a distributed process control system, includes one or more operator interfaces 214A coupled to one or more distributed controllers 214B via a bus, such as an Ethernet bus. The controllers 214B may be, for example, DeltaV™ controllers sold by Emerson Process Management of Austin, Tex. or any other desired type of controllers. The controllers 214B are connected via I/O devices to one or more field devices 216, such as for example, HART or FOUNDATION™ Fieldbus field devices or any other smart or non-smart field devices including, for example, those that use any of the PROFIBUS®, WORLD-FIP®, Device-Net®, AS-Interface and CAN protocols.

Generally, a process controller, such as process controller 212B or 214B, may communicate with a plant network system to provide information about operations under the process controller's management (e.g., field device operation) and to receive setpoint signals from the plant network system that are used in adjusting the operation of a process controller. The field devices 215 or 216 may control a physical process parameter (e.g., as an actuator in a control valve or other mechanism) or may measure a physical process parameter (e.g., as a sensor). The field devices may communicate with the controllers 212B or 214B to receive a process control signal or to provide data on a physical process parameter. The communication may be made via analog or digital signals. I/O devices, such as I/O device 212C, may receive messages from a field device for communication to a process controller or may receive messages from a process controller for a field device. The operator interfaces 214A (or 212A or 218) may store and execute tools 217, 219 available to the process control operator for controlling the operation of the process including, for example, control optimizers, diagnostic experts, neural networks, tuners, etc.

Maintenance systems may be connected to the process control systems 212 and 214 or to the individual devices therein to perform diagnostic and monitoring activities. For example, a maintenance computer 218 may be connected to the controller 212B and/or to the devices 215 via any desired communication lines or networks (including wireless or handheld device networks) to communicate with and, in some instances, reconfigure or perform other maintenance activities on the devices 215. Similarly, maintenance applications may be installed in and executed by one or more of the user interfaces 214A associated with the distributed process control system 214 to perform maintenance and monitoring functions, including data collection related to the operating status of the devices 216.

A computer system or workstation 274, which may represent any of workstations 212A, 214A, or 218, may generally include a processor 274A, a memory 274B and a display device 274C. Workstation 274 may implement any one or more of various maintenance systems and/or monitoring systems 235, business and/or management applications 243, and so on. In particular, the computer system 274 may store (e.g., using memory 274B) and implement various applications 238 and 242 (e.g., using processor 274A) to provide information to a user via the display 274C (or any other display device, such as a printer). Additionally, the computer system 274 may implement an alert/alarm application 243 responsive to one or more data transmissions sent by one or more of the liquid detection devices 10. Of course, maintenance systems and/or monitoring systems 235, alert application 243, and/or applications 238 and 242 may be executed as part of the same or different software component. A database 278 may be connected to the communication bus 245 to operate as a data historian that collects and stores configuration information as well as on-line process variable data, parameter data, status data, and other data associated with the process controllers 212B or 214B and the field devices 215 or 216 within the process plant 210. Additional plant network devices and systems may also be provided.

Generally speaking, the computers on the plant computer network (e.g., the workstation 274, the controllers 212B 214B, maintenance computer 218, and/or other computers interconnected via the bus 245 or via other computer networks in the plant) may be configured to communicate with communication nodes optionally located in the field devices 215, 216 and the wireless router 54. When any of the liquid detection devices 10, such as 10a or 10b, transmits a data signal with a message as described above to any of the communication nodes, the plant computer network is configured to re-transmit the message on to one or more of the computers, such as preferably a maintenance computer 218 or the workstation 274, where an alert, such as a warning or status message, can be provided to a plant operator or to another computer system, such as a monitoring and/or maintenance program.

For example, the alert/alarm application 243 may be used to manage and/or route alerts transmitted by one of the liquid detection devices 10 in the plant 210. In this case, when some pre-determined threshold amount of liquid is detected by one of the water sensors 22, the corresponding wireless communicator 14 transmits a corresponding data signal/message as described above. For the liquid detection device 10a, the wireless communicator 14 may be a near-field and/or low-power transmitter that transmits the signal to the wireless receiver in the immediately adjacent digital valve controller 60. The digital valve controller 60 then forwards the message to the workstation 274 via the bus 245. For the liquid detection device 10b, the wireless communicator 14 may be a longer-range transmitter that transmits the signal to the Wi-Fi router 54 which then forwards the message to the workstation 274 via the bus 245. Of course, the alert/alarm application 243 may be implemented on other computers in the plant computer network, and the wireless transmissions sent by the wireless communicators 14 may take different routes using different communication nodes and transmission routes throughout the plant, as would be understood in the art. Further, a single communication node may receive transmissions from more than one liquid detection device 10, and/or a single liquid detection device 10 may transmit to more than one communication node in the plant.

Figure 6:
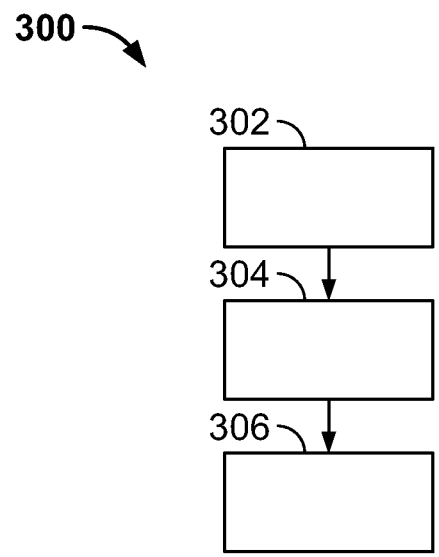
FIG. 6 illustrates a method according to aspects of the present disclosure.

FIG. 6 illustrates a basic method 300 of monitoring a pneumatic supply in a process control system for liquid with a liquid detection device 10. The liquid detection device 10 may be operatively installed in a process control system in at least any of the arrangements as described previously herein. At 302, the presence of liquid in the pneumatic supply is detected with the water sensor 22. Thereafter at 304, a wireless signal is transmitted by the wireless communicator 14, for example to one or more of the wireless communication nodes on the plant computer network. The transmitted wireless signal is indicative of the presence of liquid detected by the electronic liquid sensor 22. Optionally, at 306, the transmitted wireless signal is relayed from the communication node to a plant computer on the plant network. Thereafter, the plant computer may provide an indication, such as an alert, a warning, or other message, to a plant operator or a monitoring and/or maintenance program.

Figure 7:
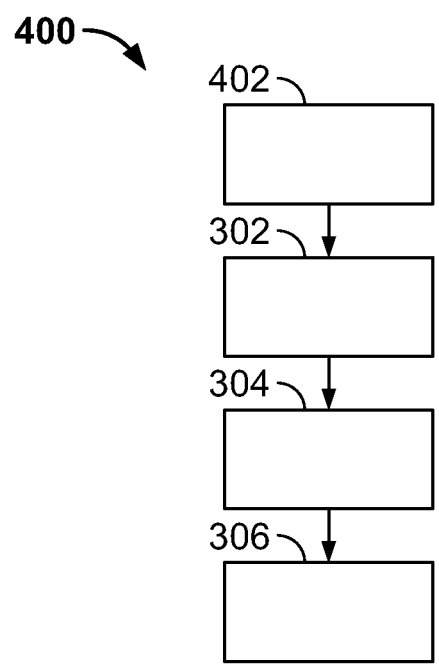
FIG. 7 illustrates a method according to additional aspects of the present disclosure.

FIG. 7 illustrates another method 400 of monitoring a pneumatic supply in a process control system for liquid that expands upon the method 300. The method 400 includes at 302 detecting the presence of liquid in the pneumatic supply with the water sensor 22 and at 304 transmitting the wireless signal with the wireless communicator 14 as described previously. In addition, the method 400 includes at 402 periodically activating the electronic liquid sensor 12 temporarily to sense for the presence of liquid in the pneumatic supply. In other words, the electronic liquid sensor 12 is periodically activated for a short period of time and then deactivated until the next time it is activated. Further, at 304 a wireless signal is transmitted each time the electronic liquid sensor is activated. Therefore, at 304 a wireless signal is transmitted both when liquid is detected by the water sensor 22 and when no liquid is detected by the water sensor 22. Under these circumstances, the wireless signal transmitted at 304 preferably differentiates between different readings obtained by the water sensor 22. For example, in some arrangements, at 304 a first message is transmitted when liquid is detected by the water sensor 22, and a second message is transmitted when liquid is not detected by the water sensor 22. In some arrangements, at 304 a first message is transmitted when no liquid is detected by the water sensor 22, a second message is transmitted when a first level of liquid is detected by the water sensor 22, and a third message is transmitted when a second level of liquid is detected by the water sensor 22. The method 400 also optionally includes at 306 relaying the transmitted wireless signal on to a computer on the plant computer network, where an alert and/or warning may be generated as described previously.

The step of periodically activating the electronic liquid sensor at 402 may be performed in any of the manners described previously herein. For example, the electronic liquid sensor 12 may be activated at a first pre-selected time interval when no liquid is detected by the water sensor 22 and may be activated at a second, faster time interval when liquid is detected by the water sensor 22. In other arrangements, the electronic liquid sensor 12 may be activated at the same pre-selected time interval regardless of whether or not liquid is detected by the water sensor 22. Furthermore, the method may include transmitting one or more various specific data transmission/messages by the wireless communicator 14 depending upon what is sensed by the water sensor 22 and/or the way the electronic liquid sensor is periodically activated, in any of the manners described previously herein.

This detailed description is to be construed as examples only and does not describe every possible embodiment, as describing every possible embodiment would be impractical, if not impossible. One could implement numerous alternate embodiments, using either current technology or technology developed after the filing date of this application. Thus, while specific exemplary forms are illustrated and described herein, it is to be understood that any of the various aspects, arrangements, and/or features disclosed herein may be combined with any one or more of the other aspects, arrangements, and/or features disclosed herein in a manner that would be understood by a person of ordinary skill in view of the teachings of this disclosure.

We claim:

1. A liquid detection device to detect and provide an indication of liquid contamination in a pneumatic supply, the device comprising:
    a housing comprising a sensor body and an electronics case fluidly sealed from the sensor body, the sensor body adapted to be exposed to the pneumatic supply;
    an electronic liquid sensor carried by the housing and configured to be coupled to the pneumatic supply and to detect the presence of liquid in the pneumatic supply; and
    a wireless communicator carried by the housing and configured to transmit data from the electronic liquid sensor to a communication node on a plant computer network,
    wherein the electronic liquid sensor comprises a water sensor configured to detect the presence and/or amount of water in the pneumatic supply, and detection circuitry connected to the water sensor and configured to detect the presence and/or amount of water detected by the water sensor,
    wherein the water sensor is disposed in the sensor body of the housing and the wireless communicator and the detection circuitry are disposed outside of the sensor body and in the electronics case of the housing, such that the wireless communicator and the detection circuitry are fluidly sealed from the water sensor.

2. The liquid detection device of claim 1, wherein the wireless communicator comprises a near-field data transmitter.

3. The liquid detection device of claim 2, wherein the near-field data transmitter comprises a high-frequency radio transmitter.

4. The liquid detection device of claim 1, wherein the wireless communicator is configured to communicate on a digital industrial automation protocol.

5. The liquid detection device of claim 1, wherein the electronic liquid sensor and the wireless communicator are carried together as a single unit by the housing.

6. The liquid detection device of claim 5, further comprising a battery power source carried by the housing and configured to power the electronic liquid sensor.

7. The liquid detection device of claim 6, wherein the electronic liquid sensor further comprises power circuitry configured to control a supply of power to the detection circuitry and the wireless communicator; and wherein the power circuitry and the battery are disposed in the electronics case of the housing fluidly sealed from the sensor body of the housing.

8. The liquid detection device of claim 1, wherein the wireless communicator is configured to transmit the data intermittently.

9. The liquid detection device of claim 8, wherein the wireless communicator is configured to transmit the data at pre-selected time intervals.

10. The liquid detection device of claim 9, wherein the electronic liquid sensor is configured to differentiate between no liquid being present and at least two different levels of liquid being present.

11. The liquid detection device of claim 10, wherein the wireless communicator is configured to transmit a first message when no liquid is present, a second message a first level of liquid is present, and a third message when a second level of liquid is present.

12. A liquid detection device to detect and provide an indication of liquid contamination in a pneumatic supply, the device comprising:
    a housing;
    an electronic liquid sensor carried by the housing and configured to be coupled to a pneumatic supply and to detect the presence of liquid in the pneumatic supply; and
    a wireless communicator carried by the housing and configured to transmit data from the electronic liquid sensor to a communication node on a plant computer network,
    wherein the electronic liquid sensor comprises a water sensor configured to detect the presence and/or amount of water in the pneumatic supply, and detection circuitry connected to the water sensor and configured to detect the presence and/or amount of water detected by the water sensor,
    wherein the water sensor is disposed in a first portion of the housing exposed to the pneumatic supply and the wireless communicator and the detection circuitry are disposed in at least one other area of the housing fluidly sealed from the first portion of the housing,
    wherein the wireless communicator is configured to transmit the data intermittently,
    wherein the wireless communicator is configured to transmit the data at pre-selected time intervals, and wherein the wireless communicator is configured to transmit the data at a first pre-selected time interval in response to the electronic liquid sensor sensing less than a threshold amount of liquid, and to transmit the data at a second, shorter time interval in response to the electronic liquid sensor sensing more than the threshold amount of liquid.

13. A process control system comprising:
a pneumatic supply line;
a wireless communication node on a plant computer network;
a sensor body fluidly coupled to the pneumatic supply line, the pneumatic supply line being at least partially disposed outside of the sensor body; and
a liquid detection device operatively coupled to the pneumatic supply line, via the sensor body, to sense the presence of liquid in the pneumatic supply line, wherein the liquid detection device comprises:
an electronic liquid sensor configured to detect the presence of liquid in the pneumatic supply line, wherein a first portion of the electronic liquid sensor is disposed in the sensor body and a second portion of the electronic liquid sensor is disposed outside of the sensor body; and
a wireless communicator configured to transmit data from the electronic liquid sensor to the wireless communication node.

14. The process control system of claim 13, wherein the wireless communication node is part of a field device configured to communicate on a digital industrial automation protocol on the plant computer network, and wherein the field device comprises a digital valve controller.

15. The process control system of claim 13, wherein the wireless communication node is not part of a field device.

16. The process control system of claim 15, wherein the wireless communication node comprises at least one of a radio frequency transceiver and a wireless router.

17. The process control system of claim 13, wherein the liquid detection device further comprises a housing comprising the sensor body and an electronics case fluidly sealed from the sensor body, wherein the electronic liquid sensor comprises a water sensor configured to detect the presence and/or amount of water in the pneumatic supply line, and detection circuitry connected to the water sensor and configured to detect the presence and/or amount of water detected by the water sensor, and wherein the water sensor is disposed in the sensor body of the housing exposed to the pneumatic supply line and the wireless communicator and the detection circuitry are disposed in the electronics case of the housing, such that the wireless communicator and the detection circuitry are fluidly sealed from the water sensor.

18. The process control system of claim 13, further comprising a pneumatic device, wherein the pneumatic supply line is configured to supply air to the pneumatic device, and wherein the sensor body has an inlet fluidly coupled to the pneumatic supply line and an outlet fluidly coupled to the pneumatic device, such that the air supplied by the pneumatic supply line flows through the sensor body and into the pneumatic device.

19. The process control system of claim 13, wherein the sensor body comprises a tube section surrounding a portion of the pneumatic supply line, the water sensor disposed inside the tube section.

20. A process control system comprising:
a pneumatic supply line;
a wireless communication node on a plant computer network;
a sensor body fluidly coupled to the pneumatic supply line, the pneumatic supply line being at least partially disposed outside of the sensor body; and
a liquid detection device operatively coupled to the pneumatic supply line, via the sensor body, to sense the presence of liquid in the pneumatic supply line, wherein the liquid detection device comprises:
an electronic liquid sensor configured to detect the presence of liquid in the pneumatic supply line, the electronic liquid sensor comprising a water sensor and detection circuitry connected to the water sensor, the water sensor disposed in the sensor body and the detection circuitry disposed outside of the sensor body; and
a wireless communicator disposed outside of the sensor body and configured to transmit data from the electronic liquid sensor to the wireless communication node, wherein the liquid detection device further comprises a battery configured to power the electronic liquid sensor and the wireless communicator.

21. A method of monitoring a pneumatic supply in a process control system for liquid, the method comprising:
operatively coupling a liquid detection device to the pneumatic supply line, the liquid detection device comprising a housing, an electronic liquid sensor carried by the housing and coupled to the pneumatic supply line and configured to detect the presence of liquid in the pneumatic supply, and a wireless communicator carried by the housing and configured to transmit data from the electronic liquid sensor to a wireless communication node of a plant computer network, wherein the housing comprises a sensor body fluidly coupled to the pneumatic supply line, the pneumatic supply line being at least partially disposed outside of the sensor body, wherein the electronic liquid sensor comprises a water sensor and detection circuitry connected to the water sensor, wherein the water sensor is disposed in the sensor body of the housing and the wireless communicator and the detection circuitry are disposed outside of the sensor body and in at least one other area of the housing fluidly sealed from the sensor body of the housing;
detecting the presence of liquid in the pneumatic supply line with the water sensor; and
transmitting with the wireless communicator a wireless signal that is indicative of the presence of liquid detected by the electronic liquid sensor to the wireless communication node on the plant computer network.

22. The method of claim 21, further comprising:
periodically activating the electronic liquid sensor temporarily to sense for the presence of liquid in the pneumatic supply; and
transmitting a wireless signal with the wireless communicator with each activation of the electronic liquid sensor.

23. The method of claim 22, further comprising:
transmitting with the wireless communicator, with each activation of the electronic liquid sensor, a first message when liquid is detected and a second message when liquid is not detected.

24. The method of claim 22, further comprising:
transmitting with the wireless communicator, with each activation of the electronic liquid sensor, a first message when no liquid is detected, a second message when a first level of liquid is detected, and a third message when a second level of liquid is detected.

25. The method of claim 21, further comprising:
relaying the transmitted signal from the communication node to a plant computer on the plant network.

26. A method of monitoring a pneumatic supply in a process control system for liquid, the method comprising
operatively coupling a liquid detection device to the pneumatic supply line, the liquid detection device comprising a housing, an electronic liquid sensor carried by the housing and coupled to the pneumatic supply line and configured to detect the presence of liquid in the pneumatic supply, and a wireless communicator carried by the housing and configured to transmit data from the electronic liquid sensor to a wireless communication node of a plant computer network, wherein the electronic liquid sensor comprises a water sensor and detection circuitry connected to the water sensor, wherein the water sensor is disposed in a first portion of the housing exposed to the pneumatic supply line and the wireless communicator and the detection circuitry are disposed in at least one other area of the housing fluidly sealed from the first portion of the housing;

detecting the presence of liquid in the pneumatic supply line with the water sensor;

transmitting with the wireless communicator a wireless signal that is indicative of the presence of liquid detected by the electronic liquid sensor to the wireless communication node on the plant computer network;

periodically activating the electronic liquid sensor temporarily to sense for the presence of liquid in the pneumatic supply; and transmitting a wireless signal with the wireless communicator with each activation of the electronic liquid sensor, wherein periodically activating the electronic liquid sensor comprises:

activating the electronic liquid sensor at a first preselected time interval when no liquid is detected, and activating the electronic liquid sensor at a second, faster time interval when liquid is detected.

* * * * *

UNITED STATES PATENT AND TRADEMARK OFFICE
CERTIFICATE OF CORRECTION

| | |
|---|---|
| PATENT NO. | : 10,890,298 B2 |
| APPLICATION NO. | : 15/258075 |
| DATED | : January 12, 2021 |
| INVENTOR(S) | : Bruce F. Grumstrup |

It is certified that error appears in the above-identified patent and that said Letters Patent is hereby corrected as shown below:

On the Title Page

At item (57), Line 13, "and" should be -- an --.

In the Specification

At Column 3, Line 13, "disposed" should be -- disposed in --.

At Column 5, Line 15, "Bluetooth." should be -- Bluetooth, --.

At Column 7, Line 40, "liquid deck text device 10." should be -- liquid detection device 10. --.

At Column 9, Line 11, "electronic liquid sensor 10" should be -- electronic liquid sensor 12 --.

At Column 9, Line 49, "electronic liquid sensor 10" should be -- electronic liquid sensor 12 --.

At Column 10, Line 9, "within than" should be -- within --.

At Column 10, Line 39, "contaminates" should be -- contaminants --.

At Column 11, Line 51, "on-line" should be -- online --.

At Column 11, Lines 58-59, "212B 214B," should be -- 212B, 214B, --.

At Column 12, Line 42, "electronic liquid sensor 22" should be -- electronic liquid sensor 12 --.

In the Claims

At Column 17, Claim 26, Line 5, "comprising" should be -- comprising: --.

Signed and Sealed this
Twenty-sixth Day of October, 2021

Drew Hirshfeld
*Performing the Functions and Duties of the
Under Secretary of Commerce for Intellectual Property and
Director of the United States Patent and Trademark Office*